United States Patent [19]

Bennett, Jr. et al.

[11] Patent Number: 4,967,760
[45] Date of Patent: Nov. 6, 1990

[54] DYNAMIC SPECTRAL PHONOCARDIOGRAPH

[76] Inventors: William R. Bennett, Jr., 424 Saint Ronan St., New Haven, Conn. 06511; Jean Bennett, 4 W. 39 St., Baltimore, Md. 21218

[21] Appl. No.: 306,137

[22] Filed: Feb. 2, 1989

[51] Int. Cl.⁵ .............................................. A61B 5/02
[52] U.S. Cl. ................................. 128/715; 128/699; 128/710
[58] Field of Search ............... 128/715, 710, 712, 711, 128/699; 364/413.06

[56] References Cited

U.S. PATENT DOCUMENTS

| | | | |
|---|---|---|---|
| 3,442,264 | 5/1969 | Levitt | 364/413.06 |
| 4,413,630 | 11/1983 | Anderson et al. | 128/712 |
| 4,458,693 | 7/1984 | Badziuski et al. | 128/715 |
| 4,549,551 | 10/1985 | Dyck et al. | 128/715 |
| 4,700,712 | 10/1987 | Schmid | 128/699 |
| 4,792,145 | 12/1988 | Eisenberg et al. | 128/715 |

*Primary Examiner*—Francis Jaworski
*Assistant Examiner*—George Manuel
*Attorney, Agent, or Firm*—Sprung Horn Kramer & Woods

[57] ABSTRACT

A system of generating a spectral phonocardiogram which summarizes time-dependent changes in the heart sounds throughout the heart cycle. The system is based on the projection of spectral surfaces of the Fourier transform of heart sounds as a function of time and is a useful diagnostic tool both for a cardiologist and a general practitioner. Permanent copies of the spectral phonocardiograms can provide useful records for monitoring the development of heart disease in a given individual. The system provides a useful means for rapid screening of large groups of people for heart disease by non-specialists in cardiology. A variant of the system provides automated computer diagnosis of the probable nature of the heart disease.

34 Claims, 10 Drawing Sheets

DYNAMIC SPECTRAL PHONOCARDIOGRAPH

BACKGROUND OF THE INVENTION

The present invention relates to phonocardiograms and in particular to an improved technique for taking spectral phonocardiograms.

The prior art has noted the potential utility of computer-based Fourier analysis of heart sounds for diagnostic purposes. However, the meager amount of previous experimental work that has been done in this area has largely been limited to average studies of first (S1) and second (S2) heart sound spectra for normal individuals. Typically, such studies have been restricted to frequencies below about 150 Hz and the utility of the approach has been severely limited by the long computing time required for Fourier analysis. In addition, the previous work has largely been limited by the noise level, inadequate dynamic range and frequency response of then-available sound detection and recording apparatus.

SUMMARY OF THE INVENTION

The present system is directed to a system for obtaining projections of spectral surfaces of the Fourier transform of heart sounds in real time on a video monitor while the physician is listening to the same sounds. This technique would result in a dynamic Spectral Phonocardiogram (SPG) which in turn would provide a sensitive method of picking out irregular sound patterns at different portions of the heart cycle as a function of frequency. Because such displays would extend the sensitivity of the human ear and supplement that sensitivity with the ability of the human eye to perform pattern recognition, it would also provide a useful supplementary auscultation tool for cardiologists, for those assessing a patient's general health, and for those learning the art of physical diagnosis. With the current availability of the echocardiogram, the most immediate applications of this method would be to provide a permanent record of the heart sound spectra which could be used comparatively to monitor the progression of heart disease in a given patient and to provide rapid screening for valvular malfunctions of large groups of people (for example, school children, factory workers, military personnel, government employees, etc.) in locations remote from a major hospital by a nurse or general physician. Indication of valvular dysfunctions would then be refered to a specialist in cardiology. Variations of the invention include methods of grade level identification and computer-automated diagnosis.

These and other features and advantages of the present invention will be seen from the following detailed description of the invention, taken with the attached drawings, wherein:

DETAILED DESCRIPTION OF THE INVENTION

Anatomy and Heart Sound Source Mechanism

Figure 1:
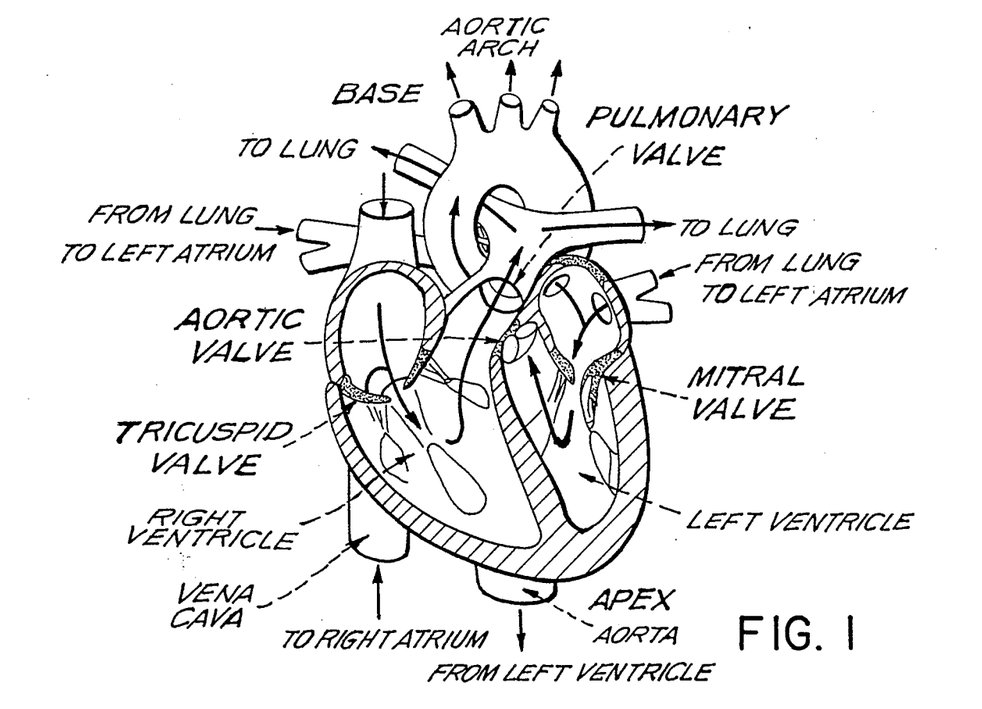
FIG. 1 is a schematic drawing of the human heart showing the basic geometry, direction of blood flow, and valve locations.

FIG. 1 shows a cross-sectional drawing of the human heart. The path of blood flow through the normal heart is shown by the heavy arrows and the four valves are indicated in large bold type. Blood flows in through the vena cava to the right atrium, through the tricuspid valve to the right ventricle, and through the pulmonary valve to the lungs. Blood returning from the lungs enters the left atrium, flows through the mitral valve to the left ventricle, and through the aortic valve to the aorta.

The "First Sound" (S1) in the heart cycle is normally strongest in the apex region, occurs when the heart contracts, and is primarily due to the near simultaneous closing of the tricuspid and mitral valves. During this contraction, blood flows from the right ventricle through the pulmonary valve to the lungs and from the left ventricle through the aortic valve to the aorta. The width of the pulse varies with spectral response function, but typically ranges from about 70 to 100 msecs with A-weighting.

The "Second Sound" (S2) is strongest in the base region, occurs when the heart expands, and is primarily due to the aortic and pulmonary valves closing. During this expansion, blood flows from the right atrium through the tricuspid valve to the right ventricle and from the left atrium through the mitral valve to the left ventricle. The width of this pulse again varies with spectral response function, but is typically about 25 to 60 msecs with A-weighting.

The separation between S1 and S2 is typically about 300 msecs. Because the unfiltered spectral components for both S1 and S2 peak below about 5 Hz, observation times in excess of 200 msecs would be required to observe the full spectra for each sound. Conversely, to observe variations in the spectral components well within the S1-S2 time interval requires filtering (such as the A- or B-weighting curves shown in FIG. 6) to remove the extreme low frequency components.

The ideal heart sound observed with A-weighting would thus consist of two smooth pulses with durations of about 80 and 40 msecs, separated by about 300 msecs over a typical 1 sec heartbeat cycle. These sounds would give rise to smoothly-shaped pulses in the frequency domain which could be well-resolved as a function of time. However, this result for the "normal" heart sound requires laminar flow of blood through the valves, heart chambers and blood vessels, as well as simultaneous closure of the two pairs of valves generating the first and second sound.

Marked departures from the "normal" heart sound spectra can arise in a variety of ways. There are characteristic recognizable patterns in the frequency domain which are analogous to those which have been previously studied in the time-domain through auscultation:

1) Non-simultaneous closure of either pair of valves. This results in a pair of pulses within S1 or S2 which shows up in a strong interference pattern in the frequency domain. This effect may arise from benign causes (e.g., the split S1 in FIG. 8) or from pathological ones which result in more complex patterns in different regions of the SPG. Because the timing between opening and closure of valves is part of the recorded data, the spectra can be used to diagnose or confirm electrodiagram findings.

2) Valvular prolapse can result in regurgitation of blood through the valve during that portion of the cycle in which the valve is supposed to be closed. This in turn results in strong turbulence in the blood flow which results in random high frequency noise components (e.g., 300 to 1000 Hz; see FIG. 9.)

Figure 10:
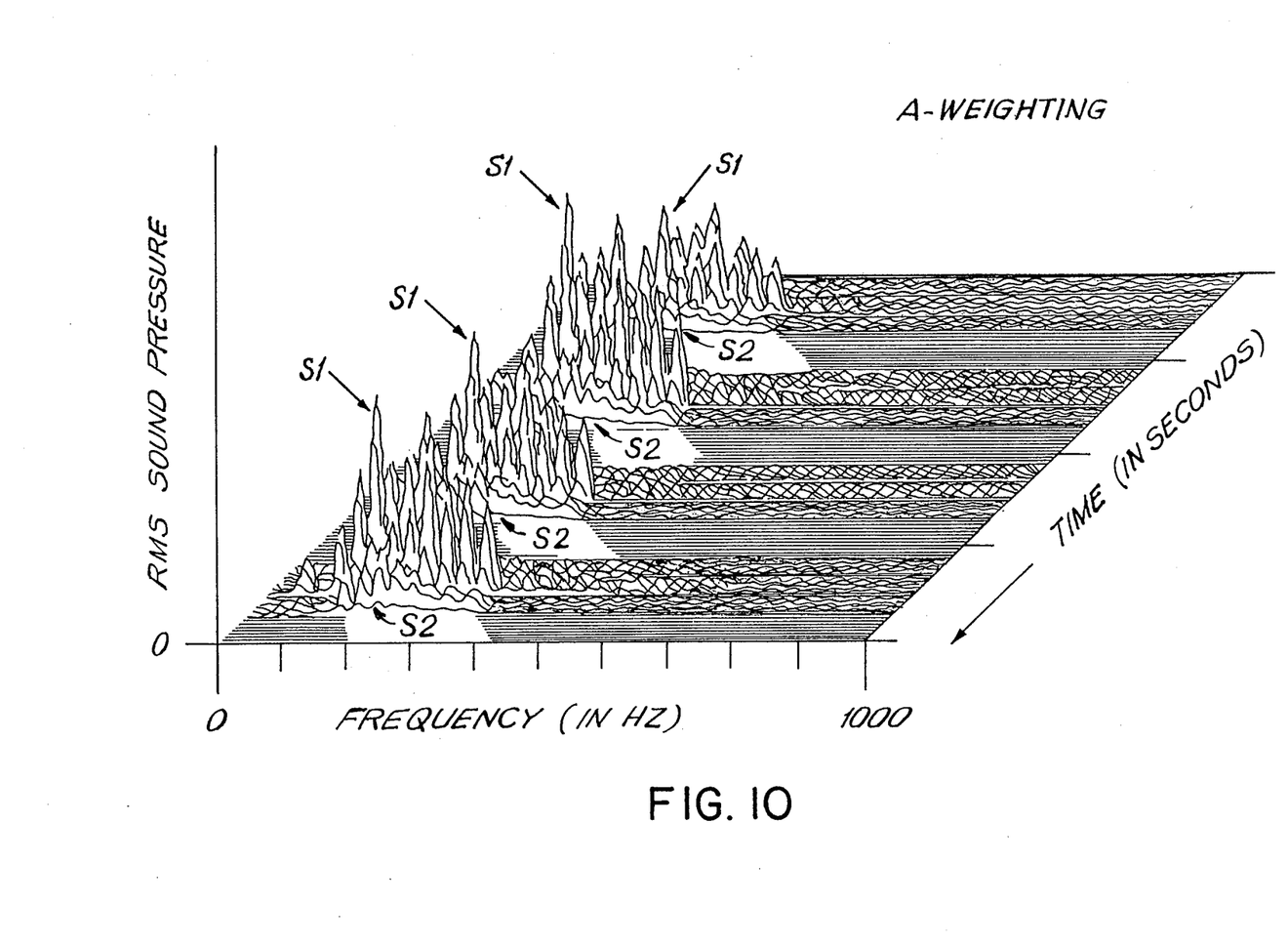
FIG. 10 is a spectral phonocardiogram of heart sounds at the base of the heart near the aortic region showing grade 3-4 out of 6 systolic murmurs from aortic stenosis and aortic regurgitation.
Figure 11:
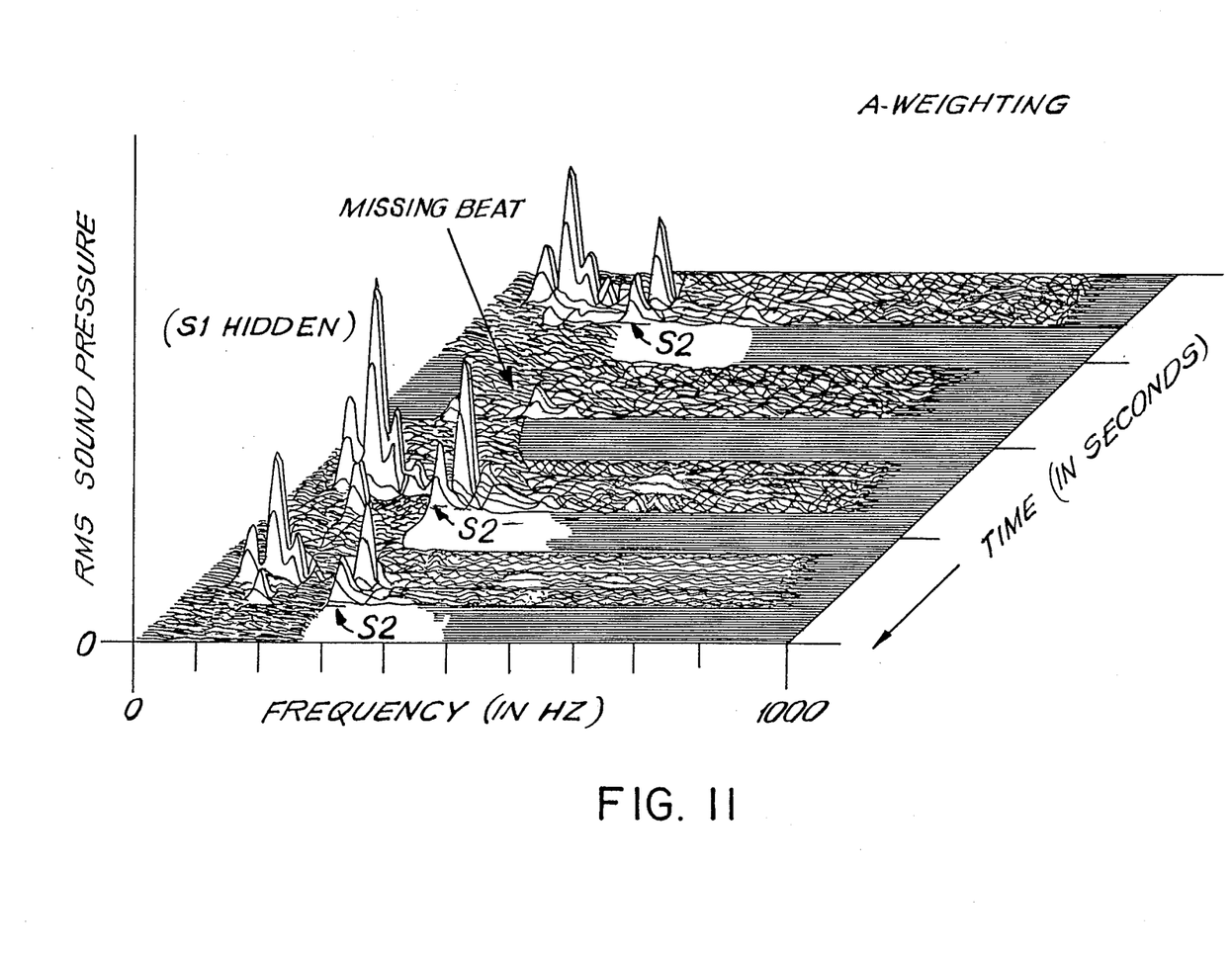
FIG. 11 is a spectral phonocardiogram of heart sounds at the aortic region with A-weighting showing a grade 5 out of 6 aortic murmur, aortic stenosis and regurgitation, chronic heart failure, and atrial fibrillation.

3) Narrowing (stenosis) of a valve or blood vessel can result in strong low-frequency pulsations ("palpable thrill") at one extreme, as well as higher-frequency turbulence (see FIGS. 10 and 11).

4) Miscellaneous: Any marked disruption in normal blood flow will produce some characteristic spectral fingerprint. For example, septal defects, systolic click, diastolic snap, pericardial knock, ejection murmurs, diastolic murmurs, and, in general, any form of valvular incompetence. It may not always be possible to diagnose the specific problem from the Spectral Phonocardiogram; however, abnormalities tend to stand out in the spectral surface plots.

Figure 2:
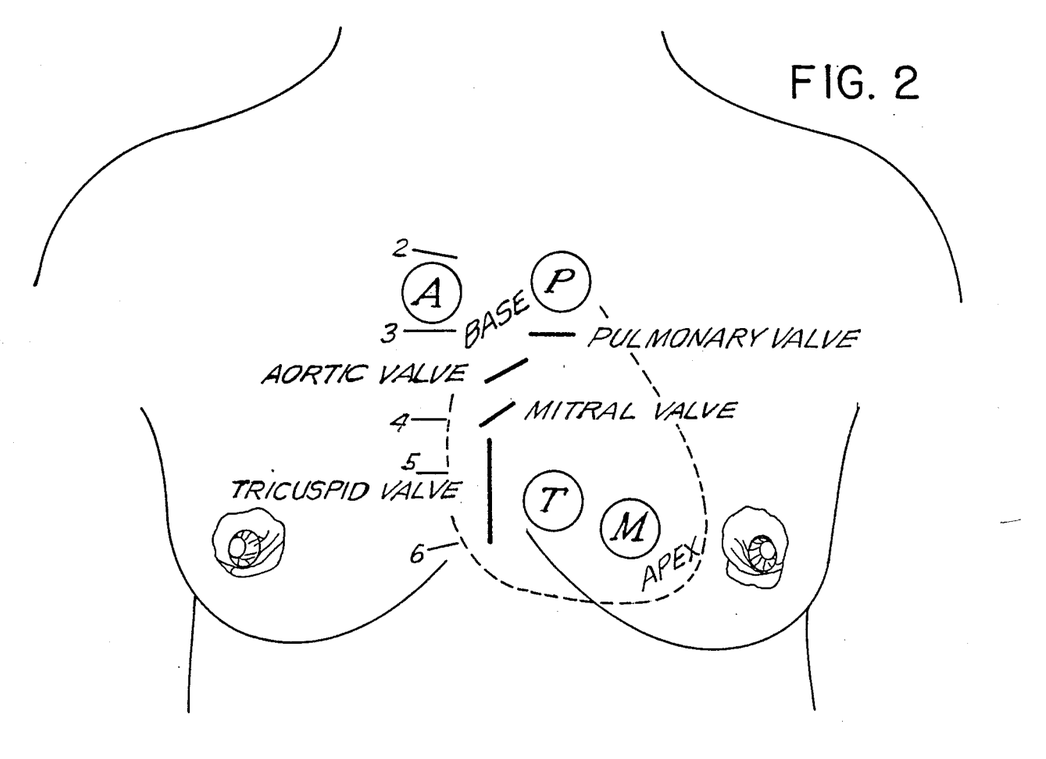
FIG. 2 is a frontal drawing of the human chest indicating orientation of the heart, the valve locations, and principal auscultation points.

FIG. 2 shows a diagram of the human (female) chest in which the heart location is indicated by a dashed line and the locations of the four valves are shown with heavy solid lines. Because of the geometry of the heart and the presence of the sternum and costal cartilage, the optimum microphone placement to detect individual valve sounds is seldom directly above the valve in question. Optimum locations for detecting the specific valve sounds are shown in the FIG. 2 by the large circles enclosing single capital letters ("A" for aortic, "P" for pulmonary, "T" for tricuspid, and "M" for mitral). The numbered short horizontal lines in the figure show the approximate locations of costal cartilages Nos. 2 through 6; the optimum locations tend to be within the corresponding intercostal spaces and on either the right (aortic) or left (pulmonary, tricuspid, and mitral) side of the sternum. Generally, mitral murmurs can be picked up selectively anywhere in the apex region.

Figure 3:
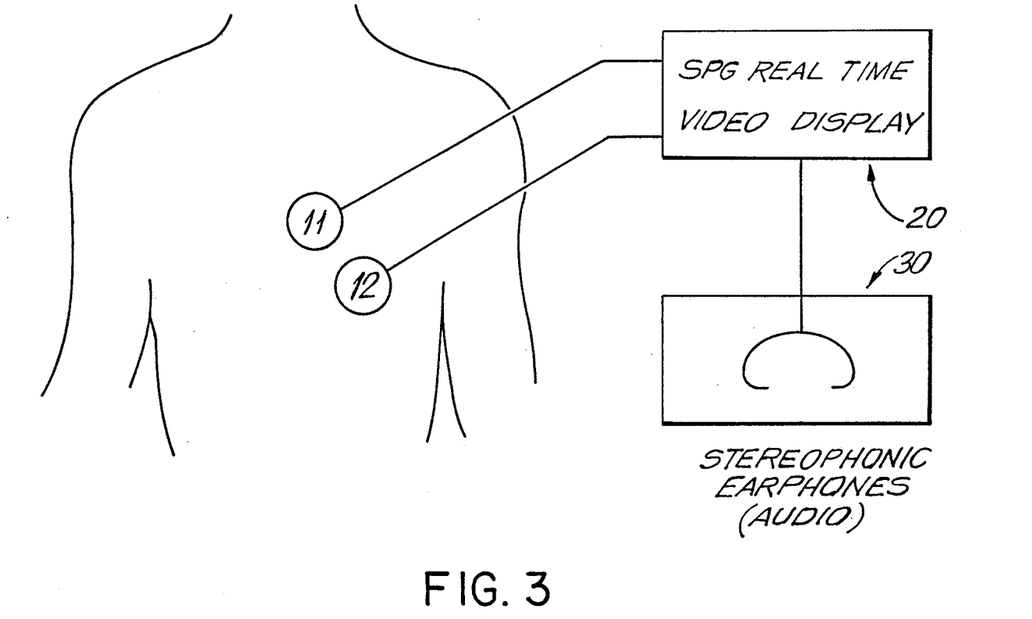
FIG. 3 is a schematic representation of the system according to the present invention.

Referring now to FIG. 3, the system according to the present invention for producing a spectral phonocardiogram includes microphones 11 and 12 placed at different regions of the chest over the heart and connected to circuitry 20 for obtaining projections of spectral surfaces of Fourier transforms of heart sounds in real time on a video monitor. Box 20 comprises elements 21-29 shown in FIG. 5. The audio signal may be heard by the attendant using stereophonic earphones 30 connected to box 20 of FIG. 3 and box 21 of FIG. 5 of the SPG (Spectral Phonocardiograph) apparatus. The earphones 30 serve as a highly sensitive electronic stethoscope for positioning the microphones 11 and 12 in FIG. 3.

The sensitive diaphragm of each microphone should be no larger than the diameter of a typical heart valve and each microphone may be positioned for optimum response from the individual valves at the positions A, P, T, and M, as indicated in FIG. 2. Listening to the heart sounds stereophonically while looking at waveform displays provides a helpful aid in identifying the physical location of unusual heart sounds and for positioning the microphones for optimum sensitivity. Under these conditions, the heart sounds appear to be spread out spatially with remarkable clarity. For example, positioning the microphones at the tricuspid (T) and mitral (M) valve regions in FIG. 2 permits identifying which of these valves closes first in the case of a split first sound, and, hence, provides a method of confirming the split-sound diagnosis.

Figure 5:
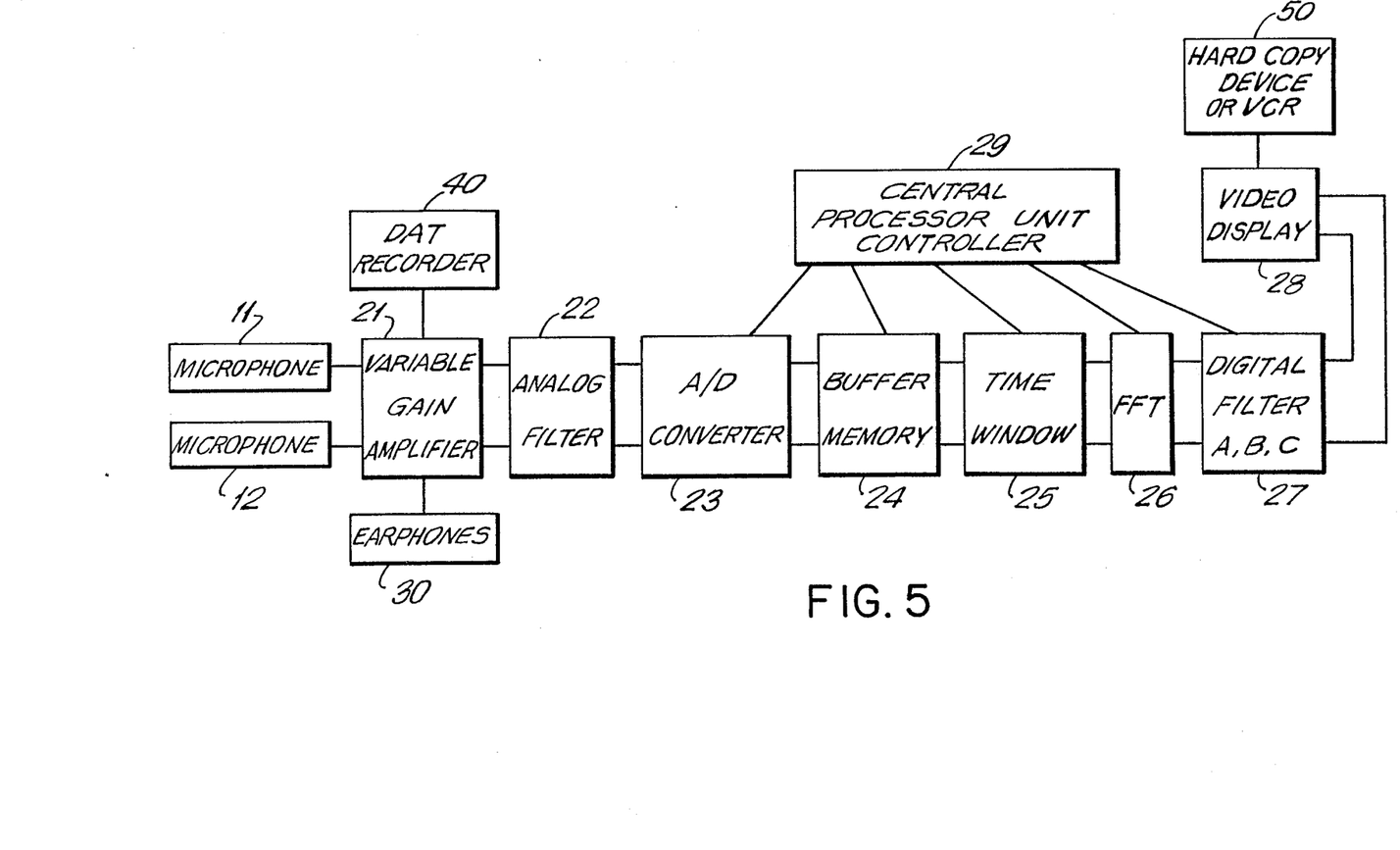
FIG. 5 is a schematic of the apparatus for carrying out the method according to the present invention.

Referring to FIG. 5, it is seen that this schematic diagram of the system depicts two parallel channels for microphone input to the final video display. These two channels function in identical manner and the flow of data through the system is indicated by the arrows. The digital circuit elements 23 through 28 utilize at least 16-bit digital signal processing (DSP) chips and are synchronized and controlled by one central processor unit (CPU) in box 29.

Analog signals from microphone 11 and 12 go through variable gain amplifier 21 and are monitored by stereophonic earphones 30 worn by the attendant. Amplifier 21 is equipped with separate gain controls and both instantaneous- and peak-reading level indicators for each amplifier so that the signals can be adjusted to optimum level without overloading the A/D converters in box 23. Optionally, these signals can be recorded with a 2-channel, 16 bit/sample digital audio tape (DAT) recorder 40 for later analysis, or re-analysis.

Referring to FIG. 5, the analog signals from amplifier 21 pass through anti-aliasing analog filter 22 which introduces a sharp attenuation characteristic amounting to about 100 dB in going from the maximum signal frequency (about 1 kHz) to be used in the spectral phonocardiograph (SPG) display to half the sample frequency (Fs) of the A/D converter 23 in accordance with the Nyquist criterion. The value of Fs can be varied somewhat but is typically about 2,550 Hz for the present application. Filter 22 eliminates spurious signals which might otherwise be produced in A/D Converter 23 by mixing signal frequency components with the sample frequency. The approximate attenuation introduced by the anti-aliasing filter is shown by the dashed curve in FIG. 6.

It will be realized that a filter which falls off by about 100 dB in going from 1,000 Hz to Fs/2=about 1275 Hz (or over a range of about 1275−1000=275 HZ =about a quarter of an octave) and is relatively constant in frequency response below 1 kHz is hard to achieve in practice without a large number of lumped circuit elements. Further, such a sharp attenuation characteristic must unavoidably introduce large frequency-dependent phase shifts throughout its pass band.

Figure 6:
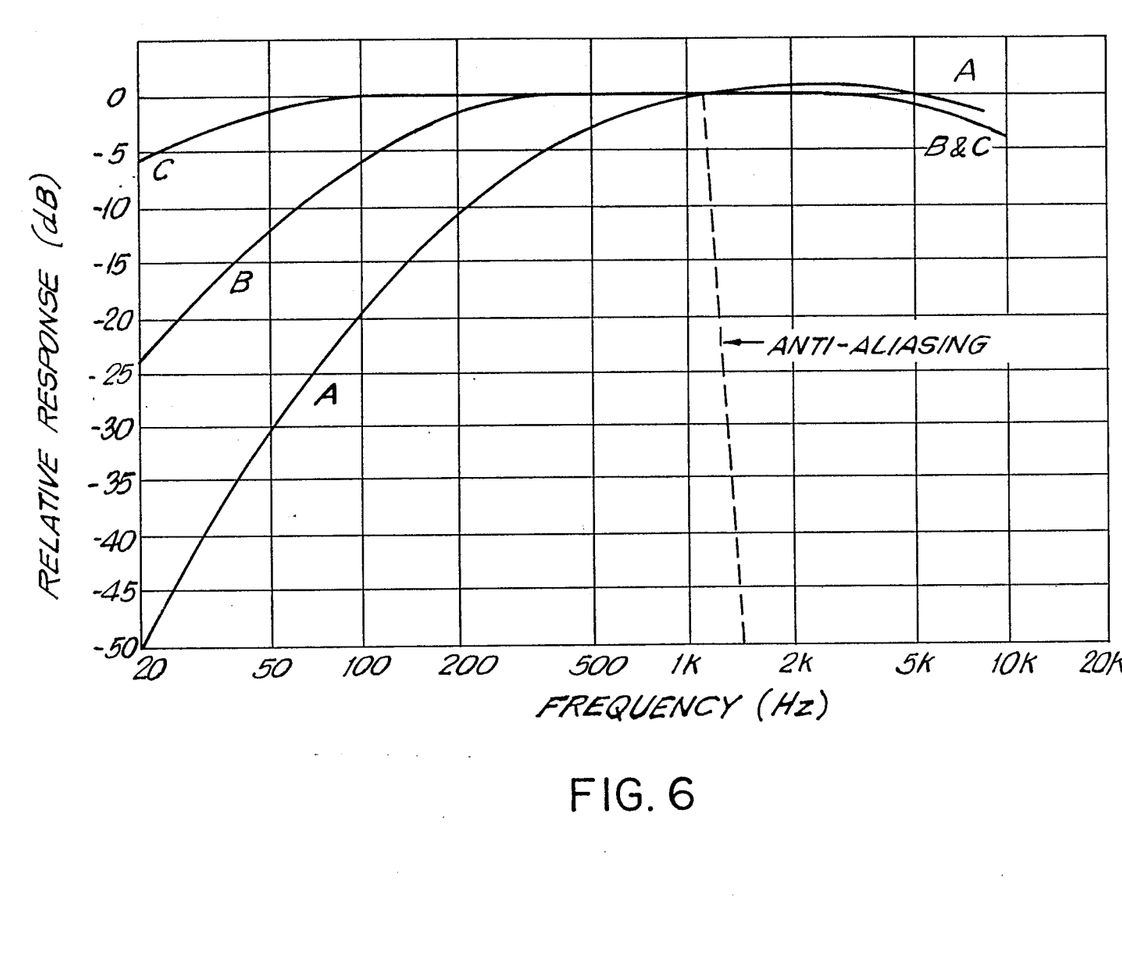
FIG. 6 is a detailed graph showing frequency response curves for A-, B-, and C-weighting and an anti-aliasing filter attenuation curve in accordance with the method of the present invention.

Alternatively, the need for such a sharp cut-off, antialiasing filter as that shown by the dashed curve in FIG. 6 can be avoided by using a technique of "oversampling". Here, instead of sampling initially at frequency Fs (=about 2,550 Hz), one samples at a much higher frequency, LFs, where L is an integer much larger than one and preferably some power of 2. For example, L=16 would be a practical value for the present application, for which the actual sample frequency would be LFs=16Fs=about 40,800 Hz. Here, in order to avoid spurious signals produced in the A/D Converter 23 by mixing signal frequency components with the sample frequency, the attenuation characteristic of the antialiasing filter only has to fall off by about 100 dB in going from 1 kHz to a frequency LFs/2=about 20,400 Hz. Hence, the 100 dB attenuation only has to occur over a range of a little more than 4 octaves (about 20,400-1,000=19,400 Hz). An analog filter with this attenuation characteristic and flat response over the pass band is much easier to construct and has substantially less phase shift over its pass band than that for the dashed curve in FIG. 6. In implementing this over-sampling technique, one then takes only one digital signal out of L (e.g., one out of 16 for L=16) coming out of the A/D converter. In this way, one regains the initially desired sample rate, Fs=about 2,550 Hz, without the difficulties presented by the steep attenuation characteristic (dashed curve) in FIG. 6. By choosing L to be a power of two, a simple binary counter driven from the actual sample frequency clock can be used to select the desired output samples.

For optimum results, A/D converter 23 (together with the rest of the digital circuit elements in boxes 24–27) should have a resolution of at least 16 bits per sample on each channel; in that case no additional filtering is required in analog filter 22 for typical signals from heart sounds. However, if the resolution of the A/D converter is significantly less than 16 bits/sample, additional low frequency filtering is required to display spectra with A- or B-weighting satisfactorily; this means adding different lumped circuit filter elements in box 22 to obtain the low frequency attenuation characteristics for the A- and B-weighting curves shown in FIG. 6.

For example, the full dynamic range over frequencies varying from 5 to 1000 Hz of a first- or second- heart sound containing a Grade 1 out of 6 murmur in the range from 200 to 1000 Hz is about 70 dB. To see the murmur with a minimum signal-to-noise ratio of about 15 dB requires a total dynamic range of about 85 dB, hence more than 14 bits/sample resolution. Thus, if data were to be analyzed using a 12 bit/sample A/D converter, additional lumped-circuit filtering would be required in box 22 to provide adequate A- and B-weighted results. However, in a more ideal system with 16-bit/sample resolution, results with smoother frequency response would be obtained merely by using an anti-aliasing filter in box 22 and by introducing A-, B-, or C-weighting curves digitally in box 27 of FIG. 5.

After A/D converter 22 in FIG. 5, the serial digital data are stored in buffer memory 24 in blocks of 1,024 points which are successively shifted by N points in the serial stream of data. To provide a synchronized real-time video display of the SPG at 30 frames/sec and to provide a resolution of M slices/sec in the spectral surface with maximum resolution (say 400 points) over the frequency domain from 0 to about 1000 Hz from a 1,024 point FFT (Fast Fourier Transform), requires very special integer relationships between N, M and Fs. We consider two useful cases:

(i) Moderately high resolution plots such as those contained in FIGS. 8-11, are achieved with a sample frequency Fs=2550 Hz, M=30 slices/sec, and 1,024 point blocks in the time domain shifted by N=85 points in the serial stream of data.

(ii) Lower resolution plots (see FIG. 12) can be obtained at 30 frames/sec, with a sample frequency Fs=2560 Hz, M=10 slices/sec, and 1,024 point blocks in the time domain shifted by N=256 points in the serial stream of data.

It will be appreciated that other solutions with different resolution may be found.

The successive blocks of 1,024 points stored in buffer memory 24 are multiplied sequentially by a 1,024 point time-window function in box 25. Ideally, this window consists of a smoothly varying multiplicative function with zero amplitude and slope at both the start and end of the time window which forces the original signal amplitude to zero at the start and end of the window without appreciably distorting the spectral amplitudes of real signals that are periodic in the window interval. The purpose of this time-window function in the present invention is two-fold: It minimizes erroneous spectral components which would be generated in the following FFT by signals which are nonperiodic over the window. In addition it permits obtaining higher (and adjustable) time resolution (at the expense of frequency resolution) in the successive slices of the surface representing the final spectral phonocardiogram. As applied to the first and second heart sounds where strong low frequency components are present, absence of such a time window function results in a large quasi-exponential decaying pedestal of spurious frequency components on log plots of the sound pressure level vs frequency, which components extend far beyond the bandwidth of the actual signal.

Figure 7:
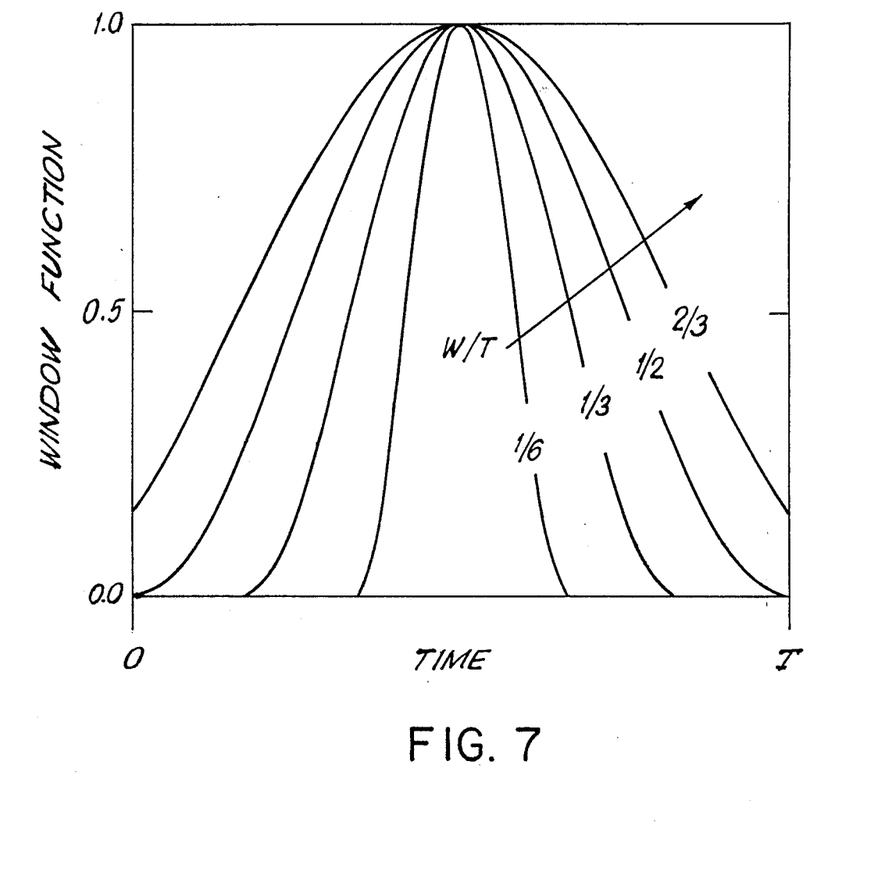
FIG. 7 illustrates a variable resolution time window function in accordance with the present invention.

FIG. 7 shows representative forms taken by an adjustable resolution time-window function in accordance with the present invention. This window function (F) has an adjustable value for its full width at half-maximum response (W) over the time interval between 0 and T and is described mathematically by:

$$F = 0.5\,[1 - \cos(\mathrm{Pi}(t - T/2 + W)/W)] \text{ for } T/2 - W < t < T/2 + W$$

and $$F = 0 \text{ otherwise,}$$

where
Pi=3.14159 . . .

The curves for this function in FIG. 7 are plotted for different values of W/T. The optimum values of the adjustable parameter range from about W=T/6 to T/2 for the present application. This time window function includes the widely-used "Hanning window" as one special case (W=T/2).

Because the FFT algorithm incorporates precisely $2^k$ points in the time domain (where k=10 provides near-optimum results for the present application), the frequency- and time-resolution determined by the number of points in the time-domain per FFT cycle can only be changed by discrete, factor-of-two jumps. These jumps are too large to provide optimum time resolution in the present application and the present adjustable time-window function provides a convenient practical means to accomplish that objective.

After multiplication by the time window in box 25, each successive block of 1,024 points in the time domain is processed by the FFT in box 26. The rate at which these FFT's are performed determines the number of slices/second generated in the real-time SPG video display. Thus, for example, considering cases (i) and (ii) enumerated above:

(i) a resolution of 30 slices/sec requires one FFT per 33 msecs in each channel;

(ii) a resolution of 10 slices/sec only requires one FFT per 100 msecs in each channel.

Real-time 16 bit 1,024 point FFT's can be performed at this speed by currently available DSP (digital signal processing) chips.

Signal in the frequency domain coming out of the FFT consists of 512 point blocks of data spread over (Fs/2) Hz, and typically the first 400 points will represent the spectrum up to about 1 kHz. These blocks of data, which now represent rms amplitudes of the spectral components, are fed sequentially to digital filter 27, where the low frequency attenuation characteristics of the A-, B- or C- weighting curves shown in FIG. 6 are stored digitally and where one pre-selected characteristic is used to multiply the frequency domain data.

The A-weighting curve is especially useful for making audio-visual comparisons of the data because the low frequency fall-off of the A-weighting curve corresponds to the attenuation of the human ear in the same frequency range. (The A-weighting curve corresponds roughly to the response of the normal ear at a loudness level of about 40 phons.) Other, less severe attenuation characteristics are desirable to study SPG patterns in the frequency range where the ear is insensitive. Although other attenuation characteristics could have been chosen arbitrarily for the present purposes, the A-, B-, and C-weighting curves shown in FIG. 6 have the virtue of being defined by the American National Standards Institute (ANSI) under standard ANSI S1.4-1983, adopted as weighting functions in sound noise-level meters. As discussed below, the low frequency attenuation of the B-weighting curve is a particularly useful compromise for quantitative determination of the grade of heart murmurs and for displaying lower frequency components in the SPG.

The blocks of frequency-domain data from digital filter 27 are presented sequentially to the video display module 28 at the slice rate desired for the final graphic display. These data are entered row-wise into a storage matrix which contains all of the frequency data to be displayed at one time. This storage matrix has a number of columns (e.g., 400) corresponding to the number of frequency components to be plotted and a number of rows (e.g., 120) corresponding to the number of slices with which the spectral surface is to be displayed. The way in which data in the storage matrix are mapped into the graphic display device determines the specific shape of the spectral surface forming the SPG.

Creating the illusion of three dimensions in this type of plot has been discussed in Chapter 3 of the book by W. R. Bennett, Jr. entitled "Scientific and Engineering Problem Solving with the Computer", (Prentice-Hall Englewood Cliffs, 1976). The illusion is produced by plotting the spectral amplitudes of each successive row of frequency-domain data from the storage matrix at positions on the display device which are shifted incrementally by amount dX in the horizontal direction and by amount dY in the vertical direction. The examples shown in FIGS. 8-11 correspond to incremental shifts of dX=2 pixels and dY=2 pixels for each successive row of 400 points, displayed using one pixel/frequency channel in the horizontal direction. Hence in this case, the time axis appears to recede at 45 degrees=arctan(-dY/dX) in respect to the horizontal.

The data entered in the first row of the storage matrix are used to initialize a "horizon array" for a hidden-line algorithm. The horizon array has a number of elements equal to the total number of pixels in the horizontal direction and the values stored in the horizon array represent the running maximum value of the absolute vertical coordinate for a particular horizontal coordinate (the array index) which has been previously plotted (including the vertical displacement, MdY, which is given to the Mth slice in creating the illusion of perspective). The horizon array is up-dated as each successive row of the matrix is plotted. If the old value stored in the horizon array is larger than the new value for that same horizontal coordinate, the new point is suppressed in the plot. Otherwise, the new point is plotted and the value for the horizon array is set equal to the new maximum vertical coordinate for that horizontal coordinate. This process results in "hiding" data points which would fall behind taller foreground structures already entered in the plot of the surface.

We outline here two basically different methods for creating a dynamic real-time SPG display from data fed into the storage matrix. For the sake of specific example and numerical comparison, we will illustrate with a 640×480 pixel format which is commonly available in high-speed color displays. We will assume the complete picture is to be refreshed at 30 Hz so that the frame rate can be synchronized with conventional video displays and VCR's (video cassette recorders). We shall also assume that 4 seconds of data are to be displayed at 30 slices/sec for a total of 4×30=120 slices in the surface and that there are 400 frequency components to be displayed. Hence, there are 120 rows and 400 columns in the storage matrix. Increments of dX=dY=2 pixels per row would permit a maximum displayed amplitude of 240 pixels per scan; i.e., for these assumptions, 400 +120×2=640 pixels are needed in the horizontal direction and 240 +120×2=480 pixels are needed in the vertical direction.

Method I) results in a continuous real-time display. Here, each block of 400 points is initially entered in the first row of a storage matrix in the display module. When a new row of 400 points is entered, the other rows are moved sequentially upward in the storage matrix, with the exception that the top row is deleted. The most recent events are then plotted in the left foreground, and the surface appears to move continuously in the diagonally upward direction. At any given instant, the entire surface displayed on the screen will portray earlier events in the background and the most recent events in the foreground. Thus, as shown in FIGS. 8-11, time advances diagonally from background to foreground in an instantaneous picture of the surface and S1 (the first sound) falls behind the second sound (S2) in any given heartbeat. At 30 frames per second, a continuous real-time display of this surface requires a total pixel plotting rate of 120×400×30=1.44-MHz per microphone channel, with 120 ×30=3600 full-screen erases per second.

Although the plotting rates required for Method I) can be achieved with some currently available plotting devices, an alternative method with less-demanding data-plotting rates is also included in the present invention.

Method II) results in a quasi-static mode of real-time display that is continuously up-dated. In this method, 400 point blocks of frequency domain data from digital filter 27 are again presented sequentially to the video display module 28 at the slice rate desired for the final graphic display. As before, the first 400 point block of frequency-domain data is entered on the first row of the storage matrix, but the successive 400 point blocks of data are directly entered in successively higher rows of this matrix. However, as each new line of data is about to be entered in the storage matrix and plotted on the display device, the display from the old row of data is erased. With some display devices, this erasure and replotting can be done on a point-by-point basis within the particular row of the storage matrix. For example, the "erasure" process might be accomplished by replotting the original data point on that row, using the same color as the background screen (e.g., by plotting white points on a white screen, or black points on a black screen) before adding the new point in a different color or gray-scale level. In this method, one only has to erase and replot 400 points in each frame. Hence in this case, a real-time display up-dated 30 times per second only requires a maximum pixel plotting rate of 2×400×30=24 kHz per microphone channel, with no full screen erasures. In this mode, when the screen is completely filled, the plot "wraps" around vertically, starts over again at the bottom of the screen, and the horizon array is reinitialized. In this case, time appears to flow diagonally from the foreground to the background and S1 (the first sound) will fall in front of the second sound (S2). In general, there will be a moving discontinuity in the plot at the row of the display where new data are being entered. However, the remainder of the surface appears static.

Although the basic properties of the SPG can be displayed using a monochrome video monitor with only one microphone channel, a simple three-color display can be used to substantial advantage. The contrast in the surface plot can be enhanced by plotting non-zero signal components in different colors from that used to depict the zero-signal background plane and the fixed scale markings. By using different colors for non-zero signals from each of the two microphone channels, a three-color display results in which the two signals from different regions of the heart are simultaneously shown in different colors. Such 3 color 2 microphone channel displays make it easier to pin-point the source of heart sound irregularities, especially when viewed while listening to the heart sounds with stereo earphones. Alternatively, different color palettes can be used on more elaborate color monitors so that the color still changes with intensity, but with different hues for each of the two microphone channels, and is still distinct from the color of the zero-signal background plane.

One can enhance some characteristics of the heart-sound spectral display by plotting a surface of the difference between the two microphone signals at box 28. This approach has the advantage that common signals (including background noise levels) from two different regions of the heart cancel out, leaving a display which exaggerates differences between these two regions. Although the optimum way to achieve this cancellation is to take the difference signal after the two signals have passed the digital filter 27, many benefits of this approach could be obtained in a less complex system by taking the difference between the two analog signals emerging from amplifier 21 and sending this difference signal through a one-channel system containing elements equivalent to those in boxes 22–28 of FIG. 5.

It should be noted that the use of 30 Hz synchronization of the sample frequency and slice-rate in the present method makes the SPG suitable for display on conventional video monitors and TV sets. Thus, permanent copies of the SPG display can easily be obtained as a function of time through use of a conventional VCR in box 50. Similarly the original sound channels could easily be added to the VCR audio input from the output of amplifier 21. However, the audio quality in the video tape would be limited by properties of the VCR itself. Unless the VCR has the capability for digital sound recording with 16 bit resolution, the audio signal on the video tape would be severely limited. Alternatively, an inverse FFT could be performed on the output from digital filter 27, fed through a D/A converter and provided to the analog audio input of the VCR; this method would retain an audio signal roughly representative of the video SPG display, but this additional complexity has not been shown in FIG. 5. Providing the entire apparatus in FIG. 5 is available, the simplest way to retain a permanent record of an individual time-dependent SPG is to make a digital recording of the initial sound with (16 bit/sample) DAT recorder 40 and play that recording back with circuit elements 22–29.

Finally, one can always "freeze" time at some point in the display from the dynamic spectral phonocardiograph and run off the display of the SPG at that point in time with any commonly available high-resolution hard copy device (e.g., graphic display printer, pen plotter, photographic copier, etc) as indicated in box 50 of FIG. 5. The 4 second onscreen display for the system discussed above would then typically permit displaying an SPG for the last four heartbeats, as illustrated in the examples below.

It will be appreciated that the availability of higher-resolution video display devices would permit preserving data over a larger block of time in one screenful, by suitable adjustment of the parameters in the digital circuit elements in FIG. 5. Alternatively, the availability of higher-resolution display monitors would permit showing the time-development of the SPG with greater resolution. For example, the use of currently available monitors containing 1280×1024 pixels (with in excess of 4 thousand to 16 million color palettes) would permit doubling the time resolution of the display over the results presented here. (This doubling is accomplished by setting dX=4 pixels instead of 2 in the surface plotting algorithm, and by doubling the data processing rates.) The principal advantage of this improvement in time resolution would be in resolving low-frequency structure between S1 and S2, which, for example, can arise from aortic stenosis.

EXAMPLES

Figure 4:
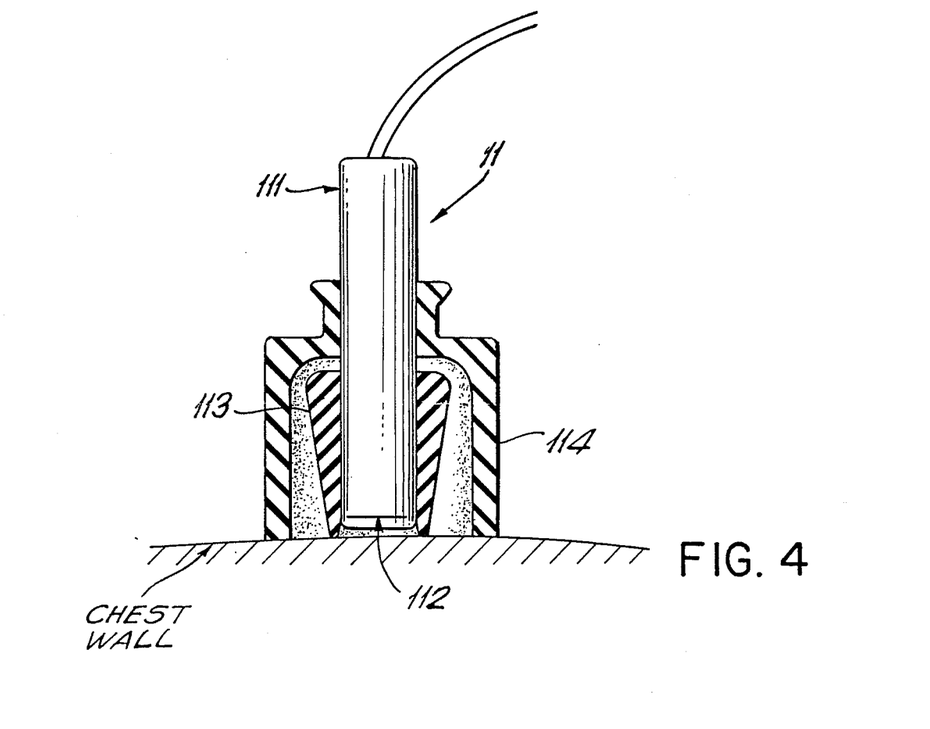
FIG. 4 is a detailed view of the apparatus for placing a microphone on a patient's body in accordance with the method of the present invention.

Measurements were made using two Sennheiser model MKH104 condensor microphones 11, 12 with frequency response curves which were flat within about 1 dB from about 5 Hz to well over 20-kHz and had absolute pressure sensitivity of about 2 mV/microbar. As shown in FIG. 4, each microphone was housed in a double rubber cup. The inner cup 113 has an inside diameter of about 2 cm and suspends the diaphragm 112 of the microphone about 5 mm above the chest wall, sealing the small enclosed volume (about 1.5 ml) from the outside and providing good acoustic coupling for the microphone to the chest wall. The outer rubber cup 114 is about 5.5 cm in diameter and provides a double acoustic shield from outside noises, as well as increasing the stability of positioning and holding the microphone. Each cup has a hole drilled in the center which fits snugly about the shaft 111 of the microphone.

These cups provide acoustic isolation so that the microphone can be positioned and held lightly in place with the fingers on top of the surface of the rubber cup 114. In this case, the double cup structure serves an additional important function of shielding the microphone from acoustic pick-up of the pulse in the attendant's fingers. Alternatively, the microphone housing can be held in place with a broad elastic belt attached to the outer cup 114 and fastened by a buckle (not shown) for extended monitoring of heart sounds.

In the measurements presented here, amplifier 21 and DAT recorder 40 in FIG. 5 consisted of a 16 bit/sample SONY PCM F1 2-channel digital recorder and associated video cassette recorder (VCR). A portable apparatus consisting of blocks 11, 12, 21, 30, and 40 in FIG. 5 was transported to Yale-New Haven Hospital where many recordings were made of patients. Some other representative cases were also studied in a quieter acoustic environment away from the hospital.

Data were taken simultaneously from the two microphones, typically, with one placed at the base of the heart (feeding the left stereo channel of the recorder and the other placed at the apex (feeding the right stereo channel). In practice, each recording was made for a period of about 5 minutes in order to provide representative data and to insure that sections of data would be recorded which were relatively free of digestive and breathing noises.

Room noise levels varied substantially in this work. Under the best conditions, even allowing 6 dB "headroom" in recording peak signals, the outside acoustic and electrical noise levels were about 85 dB to 90 dB below maximum signal at frequencies extending from 20 kHz down to about 5 Hz. However, there was substantial variation in the different hospital locations—especially in the form of low-frequency room noise generated by air conditioning systems and in some instances by radio frequency interference from fluorescent lighting.

These digital recordings were then fed into block 21 and the output of block 21 was fed into block 22 of a prototype version of the rest of the system in FIG. 5, and where it was demonstrated that the digital analysis required to produce an SPG could be done in real time. Hard copy results generated by a graphics display line printer of such SPG's (spectral phonocardiograms) are shown in FIGS. 8–11 described below.

The four examples shown were all taken with A-weighting and thus correspond to the impression that the same sounds would make on the human ear. In each case, the altitude of the spectral surface is proportional to the linear rms sound pressure amplitude of the Fourier components, frequency is displayed from about 0 to 1000 Hz along the horizontal axis, and time over a 4 sec interval is displayed by the major intervals going diagonally from the final horizon to the foreground for a continuous stream of data. The fine lines in the background plane are separated by 1/30 sec intervals and, typically, data are presented for four heartbeats for each patient. For the normal heart (FIG. 8), data of this type appear to be moderately coherent from one beat to the next and confined largely to the frequency range below about 200 to 400 Hz. The presence of a murmur often shows up as a more random fluctuation in the surface which can extend over the entire frequency domain, but is most easily noticeable for frequencies above about 400 Hz where there is relatively little amplitude in the normal heartbeat spectrum. For more severe problems, such as aortic stenosis, one sees a lot of additional structure in between S1 and S2 which frequently is strongly modulated in time.

Figure 8:
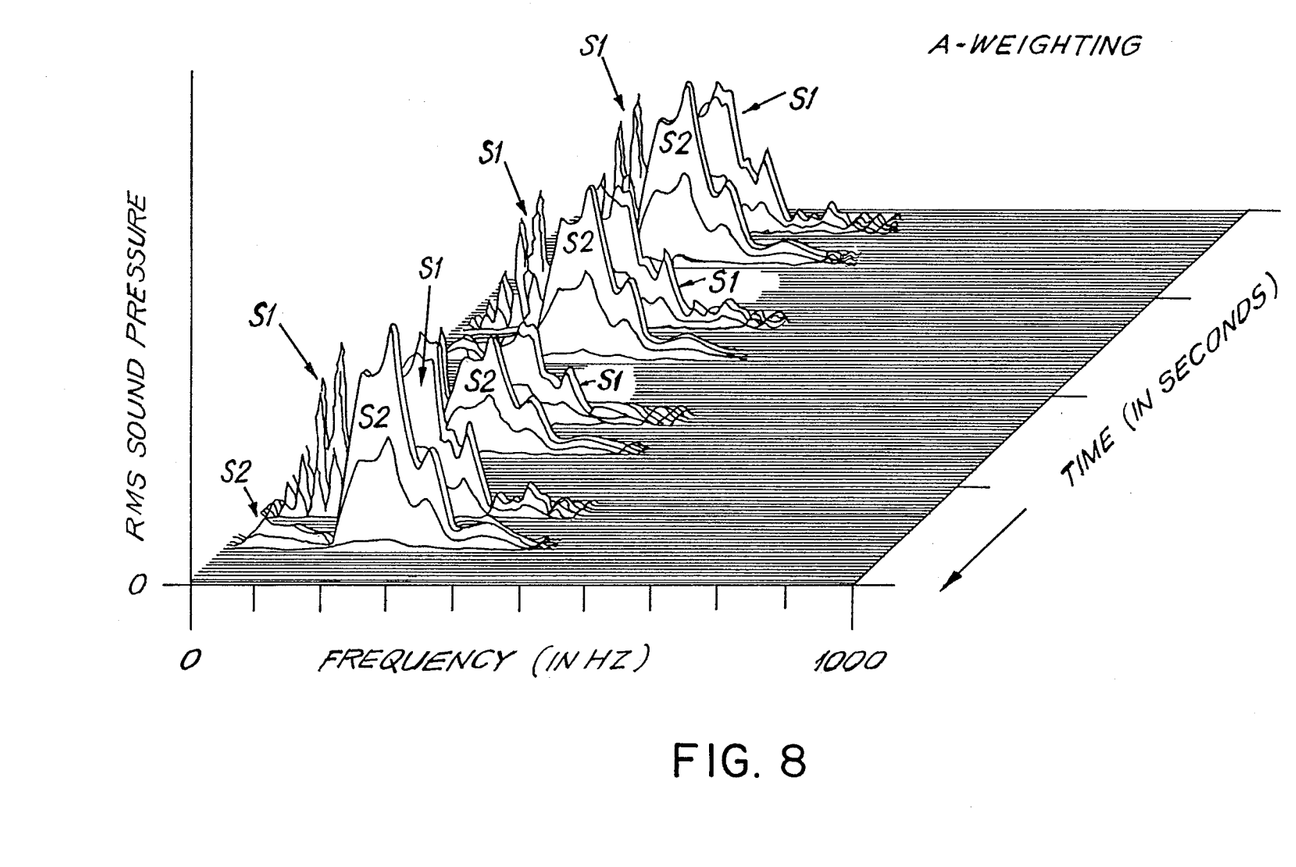
FIG. 8 is a spectral phonocardiogram at the apex of the heart with an A-weighting spectral function of a normal heart with split first sound.

FIG. 8 is a Spectral Phonocardiogram for a healthy 29 year old female taken at the apex with A-weighting. Note the extreme coherence of the spectra for the first (S1) and second (S2) sounds and the similarity of the structure from one heartbeat to the next. The absence of any significant random background to the surface and the clear isolation of the spectra for S1 and S2 indicate a complete absence of any significant heart murmurs. The strong interference pattern at frequencies around 100 Hz is somewhat unusual and arises from a marked splitting of S1. In this case, the mitral and triscupid valves closed at time intervals separated by about 35-msec and generated a strong interference pattern modulated at about 30 Hz.

Figure 9:
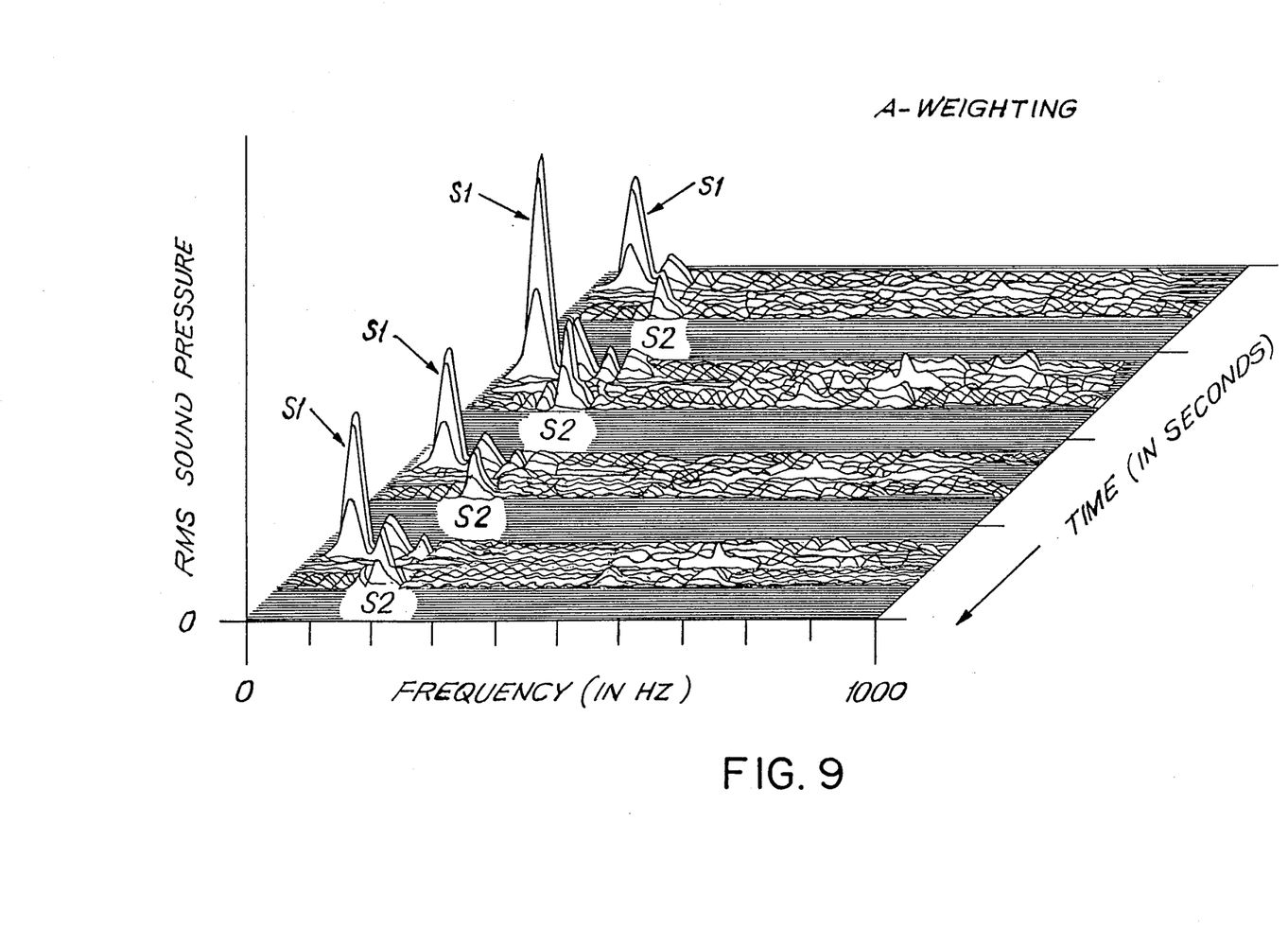
FIG. 9 is a spectral phonocardiogram of heart sounds at the apex of the heart with A-weighting and showing a grade 2 out of 6 murmur from mitral prolapse.

FIG. 9 is a Spectral Phonocardiogram taken with A-weighting at the apex of a 54 year old male with prolapse of the posterior leaf of the mitral valve. This murmur was actually discovered with the present prototype apparatus and was later diagnosed as a grade 2 out of 6 murmur from mitral insufficiency. This holosystolic murmur exhibits random spectral components that peak in the range from about 300 to 900 Hz, which arise from turbulence created by regurgitation from the mitral valve. The scraping or rasping noise one hears through the earphones in this part of the heart cycle obviously corresponds to the randomness in this portion of the spectral distribution.

FIG. 10 is a Spectral Phonocardiogram taken at the base of the heart near the aortic region for a 66 year old female suffering from aortic stenosis. It was diagnosed as a grade 3 to 4 out of 6 systolic murmur with a palpable thrill, together with a grade 1 out of 6 aortic regurgitation murmur. The maximum in the intensity distribution with A-weighting is at about 90 Hz, occurs shortly after S1, and persists for roughly half the systolic interval. Here, the spectrum has numerous peaks in frequency with a nearly uniform spacing of about 30 Hz and corresponds to the Fourier series for a quasi-periodic waveform rich in harmonic content, whose principal frequency is about 30 Hz. This seems to be a characteristic spectral fingerprint of aortic stenosis (see FIG. 11.)

FIG. 11 is a Spectral Phonocardiograph taken in the aortic region with A-weighting for a 66 year old female suffering from a large number of problems: aortic and mitral insufficiency, aortic stenosis and regurgitation with a grade 5 out of 6 aortic murmur, mitral regurgitation, chronic heart failure, and atrial fibrillation. The patient had rheumatic fever at age 12 and had been a candidate for a triple-valve replacement which was never carried out. As with FIG. 10, the mid-systolic region is marked by a series of regularly-spaced peaks that go through a maximum about ½ of the time between S1 and S2; but here, the spectrum of S1 is completely hidden by the mid-systolic structure. In this case, the Fourier series points to a quasi-periodic waveform with a fundamental frequency of about 35 Hz, which evidently is excited when blood tries to flow through the narrowed aortic valve. The granular random patterns at various times throughout the heart cycle arise from the various other valve defects summarized above.

GRADE LEVEL MEASUREMENT

Although the spectral pattern generated by the linear display of rms pressure amplitude as shown in FIGS. 8-11 provides the most useful basis to recognize the patterns from different valvular dysfunctions, a logarithmic scale provides a better basis for quantitatively judging the grade of a murmur. The currently used grading scale is based on a psycho-acoustic judgement of relative loudness of the murmur when heard through a stethoscope in which the loudness range is divided into six categories. Because of the inherent logarithmic response of the ear to loudness, the use of a Log scale in the SPG would permit defining an equivalent grade level based on a simple linear measurement from the peak intensity of the heart sound to the murmur level from a vertical scale calibrated in dB. Log plots using B-weighting and 10 dB steps in the audible spectral intensity would provide a good way to define the loudness boundaries in grade levels for two reasons: first, psychoacoustic studies have shown that people generally associate a doubling in loudness with 10-dB increments in sound pressure level; second, we have found empirically from Log plots of the SPG using B-weighting that grade "0" murmur levels (i.e., a level where the cardiologist does not detect a murmur) are typically about 60 dB down from the low frequency peak in the spectral distribution.

Figure 12:
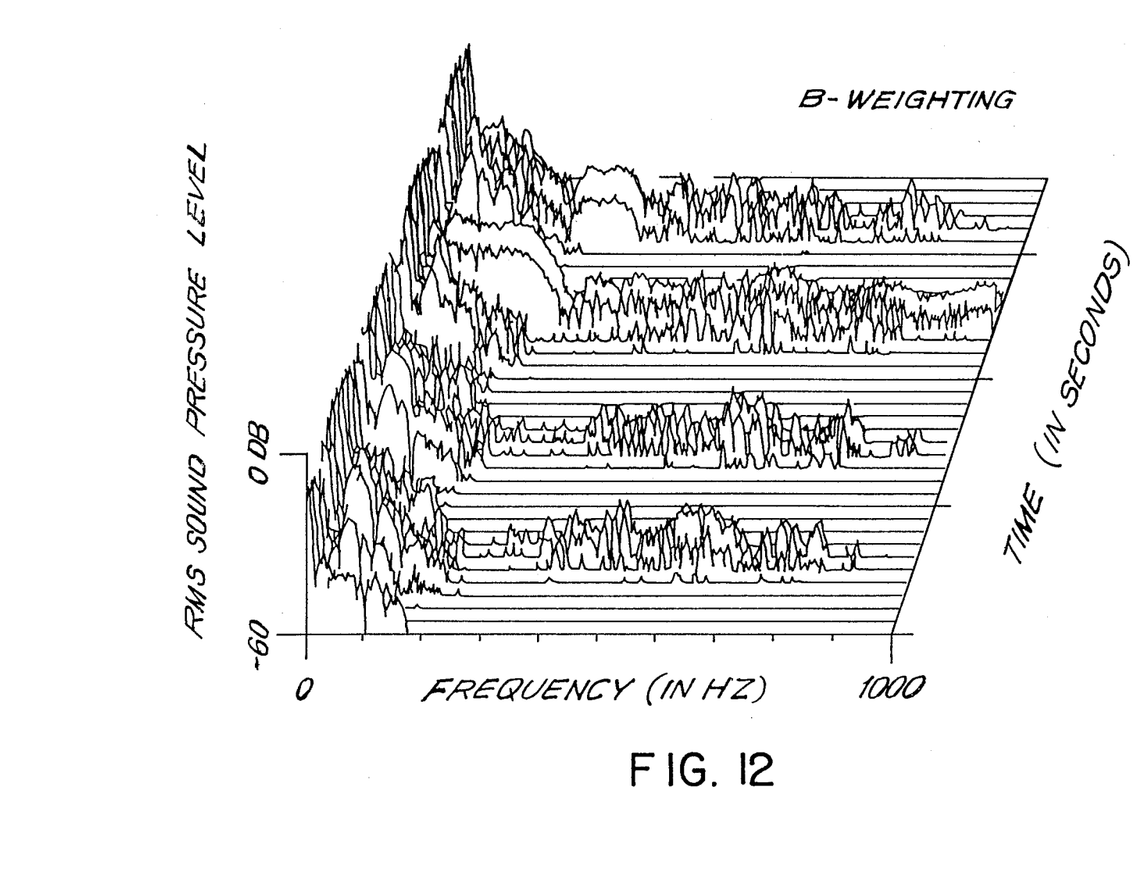
FIG. 12 is a log plot of a spectral phonocardiogram of heart sounds at the apex with B-weighting showing a grade 2 out of 6 mitral murmur which illustrates a quantitative method for grade level determination.

FIG. 12 provides a Log plot of the rms spectral amplitudes of heart sounds obtained at the apex for a grade 2 out of 6 mitral murmur using B-weighting. The vertical scale has a full range of 60 dB in this plot and one can clearly see the strong components at very low frequencies which can be used as a reference in the grade level measurement. In this case, lower time resolution has been used to portray the spectral surface at the rate of 10 slices/sec (rather than 30/sec used in FIGS. 8-11) and values of the vertical pixel increment per slice have been increased substantially to enhance the contrast. The location of the cut-off base plane on the SPG can be adjusted at different heights to optimize the ease of pattern recognition and to accomplish the murmur grade measurement itself. One can move up the cut-off plane until the murmur in the 300 to 1000 Hz spectral region just disappears visually. At that point one can read the peak height of the low frequency maximum above the murmur directly from the vertical scale in dB. For the case illustrated, one needs to move the cut-off plane up to about 20 dB out of 60 dB, in rough agreement with the 2 out of 6 grade level determined by the cardiologist.

AUTOMATED DIAGNOSIS

After an extensive catalog of characteristic spectral "fingerprints" from linear SPG plots has been accumulated, it is possible to develop an automated computer-based diagnostic method which will at least determine a minimum list of heart defects that would be implied by a particular SPG. The mathematical basis of this identification process has been discussed in a more general context in Section 2.23 of the book by W. R. Bennett, Jr., "Scientific and Engineering Problem Solving with the Computer", op. cit., Chapter 2. The method consists of the following steps:

i) expanding the unknown linear function, which consists of the pressure amplitude of the heart sound, over the time-domain of a full heart cycle, or in subdivisions of the cycle including the first sound (S1), the second sound (S2) the interval between the first and second sound (S2-S1), and the interval between the second and first sound of the next heartbeat. This expansion is done in terms of the complete set of orthonormal functions over the time interval, T, consisting of the sine and cosine functions used in the discrete Fourier transform;

ii) identifying the particular sequence of expansion coefficients (which represent the spectral amplitudes obtained by the FFT) through use of a generalized scalar product with similar sets of expansion coefficients based on previously identified, normalized patterns (i.e, the different spectral distributions characteristic of accurately diagnosed heart dysfunctions.)

Specifically, let $F_n(t)$ be the complete set of base functions which are orthonormal over the time domain $0 < t < T$. Hence, $$\int_0^T F_n(t) F_m(t) dt = \delta_{nm} \tag{1}$$

where $\delta_{nm} = 1$ for $n = m$ and $\delta_{nm} = 0$ for $n \neq m$.

A particular pattern, $V(t)$, is characterized by the spectral expansion coefficients, $C_n$, defined by $$V(t) = \sum_n C_n F_n(t) \quad \text{for } 0 < t < T \tag{2}$$

where these coefficients are given as a consequence of Eqs.(1) and (2) by $$C_m = \int_0^T V(x) F_m(t) dt. \tag{3}$$

It is desirable to normalize all of the unknown and identified pattern functions studied so that $$\int_0^T [V(t)]^2 dt = 1. \tag{4}$$

In this case, it follows from Eqs.(1)–(4) that $$\sum_m [C_m]^2 = 1. \tag{5}$$

The exact value of the normalization in Eq (5) is not important, so long as the same normalization is used for all patterns analyzed. The important thing is that the generalized vectors corresponding to the different pattern functions all be of the same length. Identification of a particular unknown pattern distribution $V(t)'$ amounts to finding a particular, known subset of expansion coefficients $C_m$ such that $$C'_m = C_m$$

within some arbitrarily chosen degree of accuracy for each member m of the subset, where $C'_m$ is determined by substituting $V'(t)$ in Eq. (3). This process may be automated by defining a set of normalized expansion coefficients $C_{m,k}$ for each identified pattern, $V_k(t)$, and by then computing the set of generalized scalar products $$S = \int_0^T V(t)V_k(t)dt = \sum_n C_m'C_{m,k}$$

for the different values of k, where k labels a particular known pattern. That value of k which provides the maximum value for S in Eq (7) then represents the best possible identification of the unknown pattern distribution in terms of the previously identified set.

This entire identification process is implemented through the use of a FFT to determine the expansion coefficients. In this case, the number of points in the FFT and the adjustable width for the time window function may be optimized for the computer-diagnostic process. A look-up table of these expansion coefficients for the previously identified patterns would be stored in the computer memory in order to perform the identification. This computer-automated diagnostic process does not actually require the real-time graphic display apparatus and could be implemented by itself in a much smaller electronic package. Alternatively, the automated diagnostic method can supplement the graphic display of the SPG.

It will be appreciated that the instant specification, examples and claims are set forth by way of illustration and not limitation, and that various modifications and changes may be made without departing from the spirit and scope of the present invention.

What is claimed is:

1. A method of producing a dynamic spectral cardiogram for picking out irregular sound patterns at different portions of a heart cycle as a function of frequency, comprising steps of:
   a. producing real-time audio representation of a patient's heart sounds; and
   b. producing a three dimensional video display of the same heart sounds by generating projections of spectral surfaces of Fourier transforms of the heart sounds in real time.

2. The method according to claim 1, wherein the real time audio representation is produced by placing at least one microphone in the vicinity of a patient's heart.

3. The method according to claim 1, wherein the video display is produced by placing at least one microphone in the vicinity of a patient's heart to produce analog output signals corresponding to heart sounds, converting the analog output signals of the microphone to digital signals, performing a fast Fourier transform on the digital signals, and displaying the transforms as spectral surfaces on a display.

4. The method according to claim 3, wherein the step of producing the video display further comprises applying an adjustable resolution time-window weighting function, F, over a time interval of duration, T, to the digital signals, wherein F is described by $$F=0.5[1-\cos(Pi(t-T/2+W)/W)] \text{ for } T/2-W<t<T/2+W$$

and F=0 otherwise, where
Pi=3.14159... and W ranges from about T/6 to T/2; and applying a second weighting function as a digital filter to the fast Fourier transform before displaying same.

5. The method according to claim 4, wherein the second weighting function is an A-weighting function.

6. The method according to claim 4, wherein the second weighting function is a B-weighting function.

7. The method according to claim 4, wherein the second weighting function is a C-weighting function.

8. A method of producing a spectral cardiogram, comprising: generating projections of spectral surfaces of Fourier transforms of heart sounds in real time, and displaying the spectral surfaces in a three dimensional display.

9. The method according to claim 8, wherein the projections are generated by placing at least one microphone in the vicinity of a patient's heart to produce an analog output signal corresponding to heart sounds, converting the analog output signal to a digital signal, and performing a fast Fourier transform on the digital signal.

10. The method according to claim 9, wherein the step of generating the projections further comprises storing the digital signal on a video tape recorder.

11. The method according to claim 9, wherein the step of generating the projections further comprises storing the analog signal on a digital audio tape recorder.

12. The method according to claim 9, wherein the step of generating projections further comprises applying an adjustable resolution time-window weighting function, F, to the digital signal over a time-window of duration T, wherein F is described by $$F=0.5 [1-\cos(Pi(t-T/2+W)/W)] \text{ for } T/2-W<t<T/2+W$$

and F=0 otherwise, where
Pi=3.14159... and W ranges from about T/6 to T/2; and applying a second weighting function to the fast Fourier transform before displaying same.

13. The method according to claim 12, wherein the second weighting function is an A-weighting function.

14. The method according to claim 12, wherein the second weighting function is a B-weighting function.

15. The method according to claim 12, wherein the second weighting function is a C-weighting function.

16. The method according to claim 8, wherein the step of displaying comprises displaying on a video monitor.

17. The method according to claim 8, wherein the step of displaying comprises displaying on a hard copy device.

18. A method of producing a dynamic spectral cardiogram for picking out irregular sound patterns at different portions of a heart cycle as a function of frequency, comprising:
   a. means for producing a real-time audio representation of a patient's heart sounds;
   b. means for producing real time Fourier transforms of the audio representation of the heart sounds; and
   c. means for producing a three dimensional video display of the same heart sounds by generating projections of spectral surfaces in real time of the Fourier transforms of the audio representation of the heart sounds 19. The device according to claim 18, wherein the means for producing real time audio representation comprises at least one microphone adapted to be placed in the vicinity of a patient's heart.

20. The device according to claim 18, wherein the means for producing the video display comprises at least one microphone adapted to be placed in the vicinity of a patient's heart to produce analog output signals corresponding to heart sounds, means for converting the analog output signals of the microphone to digital signals, means for performing a fast Fourier transform on the digital signals, and means for displaying the transforms as spectral surfaces on a display.

21. The method according to claim 20, wherein the means for producing the video display further comprises means for applying an adjustable resolution time-window weighting function, F, over a time interval of duration, T, to the digital signals, wherein F is described by $$F=0.5[1-\cos(Pi(t-T/2+W)/W)] \text{ for } T/2-W<t<T/2+W$$

and F=0 otherwise, where

Pi=3.14159... and W ranges from about T/6 to T/2; and means for applying a second weighting function as a digital filter to the fast Fourier transform before displaying same.

22. The device according to claim 21, wherein the second weighting function is an A-weighting function.

23. The device according to claim 21, wherein the second weighting function is a B-weighting function.

24. The device according to claim 21, wherein the second weighting function is a C-weighting function.

25. A device for producing a spectral cardiogram, comprising: means receptive of audio representations of hear sounds for generating Fourier transfers thereof in real time, means for generating projections of spectral surfaces of the Fourier transforms of the Fourier transforms of the heart sounds in real time, and means for displaying the spectral surfaces in a three dimensional display.

26. The device according to claim 25, wherein the means for generating the projections comprises at least one microphone adapted to be placed in the vicinity of a patient's heart to produce an analog output signal corresponding to heart sounds, means for converting the analog output signal to a digital signal, and means for performing a fast Fourier transform on the digital signal.

27. The device according to claim 26, wherein the means for generating the projections further comprises means for storing the digital signal on a video tape recorder.

28. The device according to claim 26, wherein the menas for generating the projections further comprises means for storing the analog signal on a digital audio tape recorder.

29. The device according to claim 26, wherein the means for generating projections further comprises means for applying an adjustable resolution time-window weighting function, F, to the digital signal over a time-window of duration T, wherein F is described by $$F=0.5 [1-\cos(Pi(t-T/2+W)/W)] \text{ for } T/2-W<t<T/2+W$$

and F=0 otherwise, where

Pi=3.14159... and W ranges from about T/6 to T/2; and means for applying a second weighting function to the fast Fourier transform before displaying same.

30. The device according to claim 29, wherein the second weighting function is an A-weighting function.

31. The device according to claim 29, wherein the second weighting function is a B-weighting function.

32. The device according to claim 29, wherein the second weighting function is a C-weighting function.

33. The device according to claim 25, wherein the means for displaying comprises a video monitor.

34. The device according to claim 25, wherein the means for displaying comprises a hard copy device.

* * * * *